United States Patent [19]

Sasse et al.

[11] Patent Number: 4,898,608
[45] Date of Patent: Feb. 6, 1990

[54] PYRIDYLTHIO-ACYLANILIDE HERBICIDES

[75] Inventors: Klaus Sasse, Bergisch-Gladbach; Reiner Fischer, Monheim; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 38,700

[22] Filed: Apr. 15, 1987

[30] Foreign Application Priority Data

May 2, 1986 [DE] Fed. Rep. of Germany ....... 3614846

[51] Int. Cl.[4] .................. C07D 213/57; C07D 213/64; A01N 43/40
[52] U.S. Cl. ........................................ 71/94; 546/288; 546/291
[58] Field of Search ...................... 546/288, 291; 71/94

[56] References Cited

U.S. PATENT DOCUMENTS 3,250,775  5/1966  Brokke ............................... 544/315

FOREIGN PATENT DOCUMENTS 2501648  7/1975  Fed. Rep. of Germany ...... 546/291

OTHER PUBLICATIONS

Derwent Japanese 22.5.67–17.5.67, vol. 6, No. 19.
Agricultural Chemistry, J5 5122-763.
Agricultural Chemistry, J5 6123-970.
Agricultural Chemistry, J5 6029-576.

Primary Examiner—Alan L. Rotman
Attorney, Agent, or Firm—Sprung, Horn, Kramer & Woods

[57] ABSTRACT

Novel herbicidally active pyridylthio-acylanilides of the formula

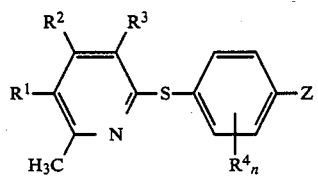

in which $R^1$, $R^2$ and $R^3$, independently of one another, represent hydrogen, halogen, cyano or trifluoromethyl or alkyl, alkoxy and alkylthio having 1 to 4 carbon atoms in each case, $R^4$ represents halogen, methyl or methoxy, n represents a number 0, 1 or 2, z represents the group (Ia)

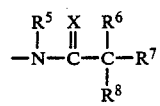

or the group (Ib)

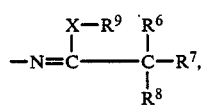

where X represents oxygen, sulphur, an N—$R^{10}$ or N—O—$R^{11}$ group, or X and $R^g$ together represent the

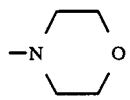

radical, and the other radicals can have various meanings.

Intermediates of the formulae

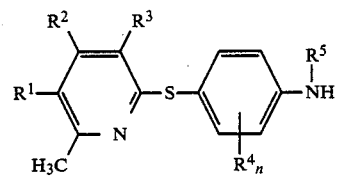

and

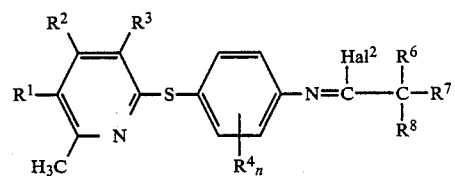

are also new.

9 Claims, No Drawings

PYRIDYLTHIO-ACYLANILIDE HERBICIDES

The present invention relates to new pyridylthioacylanilides, several processes for the preparation thereof, and the use thereof as herbicides.

It is already known that certain carboxanilides have herbicidal properties (cf. R. Wegler "Chemie der Pflanzenschutz- und Schadlingsbekampfungsmittel" [Chemistry of Plant-Protecting Agents and Pesticides], vol. 2, pages 311–314, Springer-Verlag, Berlin 1970). Thus, for example, 3′,4′-dichloropropionanilide can be employed for combating weeds. However, the herbicidal action of this compound against weeds, and also its compatibility towards important crop plants, is not always completely satisfactory in all fields of application.

It is furthermore known that numerous pyrimidin-2-yl ethers and thio ethers are suitable as herbicides (cf. Japanese Published Specification No. 9,474/1967, U.S. Pat. Nos. 3,126,271 and 3,250,775). For example, 2-phenoxy-4,6-dimethyl-pyrimidine and 2-(4-chloro-benzylthio)-4,6-dimethyl-pyrimidine can be used for combating weeds. However, the herbicidal potency of these substances is not always adequate.

It is furthermore known that lower acyl derivatives of 4-pyridyloxy- (or thio)-anilines have herbicidal properties (cf. DE-OS (German Published Specification) No. 2,501,648, Japanese Published Specification Nos. 55-122,763 and 56-123,970). In addition, herbicidally active acyl derivatives of 4-pyrimidyloxy-anilines which are substituted in the 5-position of the pyrimidyl radical by halogen or trifluoromethyl, but, on the other hand, contain no substituents in the 4-and 6-positions, are also known (cf. Japanese Published Specification No. 56-029,576). However, the activity of these substances is also not always satisfactory.

New substituted carboxanilides of the formula (I),

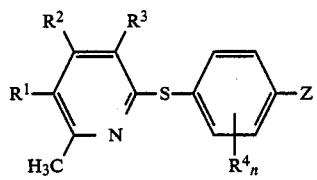

in which
$R^1$, $R^2$ and $R^3$, independently of one another, represent hydrogen, halogen, cyano or trifluoromethyl or alkyl, alkoxy and alkylthio having 1 to 4 carbon atoms in each case,
$R^4$ represents halogen, methyl or methoxy,
n represents a number 0, 1 or 2,
Z represents the group (Ia)

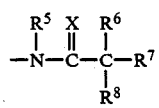

or the group (Ib)

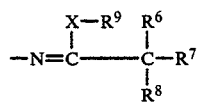

where
X represents oxygen, sulphur, an $N-R^{10}$ or $N-O-R^{11}$ group, where
$R^{10}$ and $R^{11}$, independently of one another, represent hydrogen or optionally substituted alkyl having 1 to 6 carbon atoms, or alkenyl or alkinyl having 2 to 6 carbon atoms in each case $R^5$ represents hydrogen or optionally substituted alkyl having 1 to 6 carbon atoms, or in each case optionally substituted alkenyl or alkinyl having 2 to 6 carbon atoms in each case,
$R^6$ represents hydrogen, halogen, cyano, optionally substituted alkyl having 1 to 6 carbon atoms, alkenyl having 2 to 6 carbon atoms, in each case optionally substituted aryl or aralkyl, or the $-OR^{12}$ or $-S(O)_m-R^{12}$ radicals, where
$R^{12}$ represents optionally substituted alkyl having 1 to 6 carbon atoms or optionally substituted aryl, and
m represents a number 0, 1 or 2,
$R^7$ and $R^8$, independently of one another, represent halogen or optionally substituted alkyl having 1 to 6 carbon atoms,
$R^9$ represents optionally substituted alkyl having 1 to 6 carbon atoms, or alkenyl or alkinyl having 3 to 6 carbon atoms in each case, or
$R^6$ and $R^7$ or $R^6$ and $R^8$, together with the neighbouring carbon atom, represent an optionally substituted, saturated or unsaturated ring, having 3 to 8 ring atoms, which, apart from carbon atoms, may also contain oxygen and sulphur atoms as ring members, or
$R^5$ and $R^7$ or $R^5$ and $R^{10}$ or $R^7$ and $R^9$ or $R^8$ and $R^9$ or $R^7$ and $R^8$ together represet an alkylene chain having 2 to 6 carbon atoms or an alkenylene chain having 2 to 6 carbon atoms, which may in each case be substituted by halogen, $C_1$-$C_4$-alkyl or $C_1$-$C_4$-alkoxy, or
$R^5$ and $R^{11}$ together represent an alkylene chain having 1 to 5 carbon atoms or an alkenylene chain having 2 to 5 carbon atoms, which may in each case be substituted by halogen, $C_1$-$C_4$-alkyl or $C_1$-$C_4$-alkoxy, or
X and $R^9$ together represent the

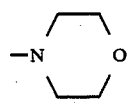

radical, have now been found.

It has furthermore been found that pyridylthioacylanilides of the formula (I) are obtained when
(a) aniline derivatives of the formula (II),

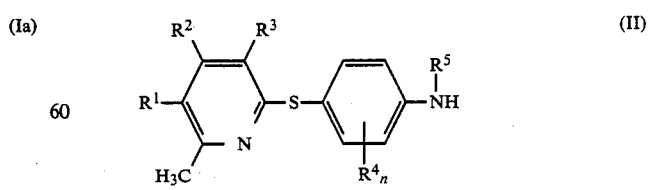

in which $R^1$, $R^2$, $R^3$, $R^4$, $R^5$ and n have the abovementioned meaning,
are reacted with carboxylic acid derivatives of the formula (III),

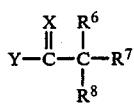

in which
R[6], R[7], R[8] and X have the abovementioned meaning, and
Y represents hydroxyl, halogen, acyloxy, alkoxycarbonyloxy or aryloxycarbonyloxy, alkyl- or arylsulphonyloxy, or the group

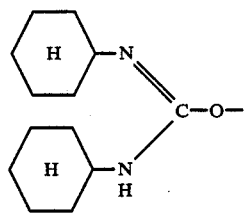

if appropriate in the presence of a diluent and if appropriate in the presence of an acid-binding agent or dehydrating agent, or when
(b) pyridine derivatives of the formula (IV),

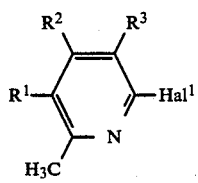

in which
R[1], R[2] and R[3] have the abovementioned meaning, and
Hal[1] represents halogen,
are reacted with acylaniline derivatives of the formula (Va) or (Vb),

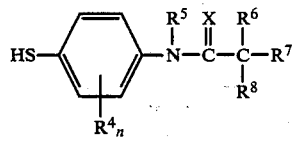

or

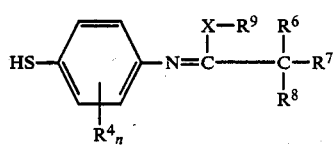

in which R[4], R[5], R[6], R[7], R[8], R[9], X and n have the abovementioned meaning,
in the presence of a diluent and if appropriate in the presence of an acid acceptor, or when
(c) carboxanilides of the formula (I), in which
R[5] represents hydrogen and
R[1], R[2], R[3], R[4], R[6], R[7] R[8], x and n have the abovementioned meaning,
are reacted with an alkylating agent of the formula (VI)

R[5]—Y[1]   (VI)

in which
R[5] has the abovementioned meaning and
Y[1] represents haloge, alkylsulphonyloxy or arylsulphonyloxy,
if appropriate in the presence of a base and if appropriate in the presence of a diluent, or when
(d) carboxylic acid imide halides of the formula (VII),

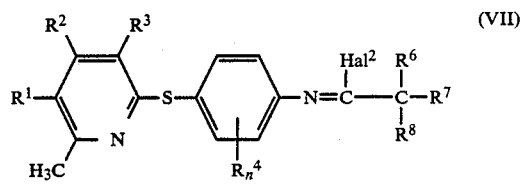

in which
R[1], R[2], R[3], R[4], R[6], R[7], R[8] *l*, and n have the abovementioned meaning and
Hal[2] represents chlorine or bromine,
are reacted with a nucleophile of the formula (VIII),

HX—R[9]   (VIII)

in which R[9] and X have the abovementioned meaning,
if appropriate in the presence of an acid-binding agent and if appropriate in the presence of a solvent, or when
(e) carboxanilides of the formula (Ic),

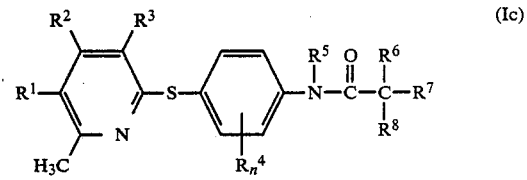

in which R[1], R[2], R[3], R[4], R[5], R[6], R[7], R[8], and n have the abovementioned meaning,
are reacted with sulphurizing reagents, such as phosphorus-(V) sulphide or 2,4-bis-(4-methoxyphenyl)-2,4-dithiono-1,3,2,4-dithiaphosphetane (Lawesson reagent), if appropriate in the presence of a solvent.

Finally, it has been found that the new pyridylthio-acylanilides of the formula (I) are distinguished by an excellent herbicidal activity.

Surprisingly, the pyridylthio-acylanilides of the formula (I) have significantly better herbicidal properties than the constitutionally most similar substances known previously. Thus, the carboxanilides of the formula (I) according to the invention can be used significantly better for combating weeds than 2-phenoxy-4,6-dimethylpyrimidine, which is a structurally similar, previously known active compound of the same mode of action.

In the context of the definitions of these substituents, in each case:
alkyl represents a straight-chain or branched carbon chain;
alkoxy represents a straight-chain or branched carbon chain;
alkylthio represents a straight-chain or branched carbon chain;
alkenyl represents a straight-chain or branched carbon chain;

alkinyl represents a straight-chain or branched carbon chain;

aryl represents an aromatic hydrocarbon radical having 6 to 14 carbon atoms, particularly having 6 to 10 carbon atoms;

aralkyl represents a phenyl radical which is bonded via an alkyl chain having 1 to 4 carbon atoms; and halogen represents fluorine, chlorine, bromine and iodine.

The pyridylthio-acylanilides according to the invention are generally defined by the formula (I).

Preferred compounds of the formula (I) are those in which $R^1$, $R^2$ and $R^3$, independently of one another, represent hydrogen, fluorine, chlorine, bromine, cyano or trifluoromethyl, or alkyl, alkoxy or alkylthio having 1 to 4 carbon atoms in each case, $R^4$ represents fluorine, chlorine, bromine, methyl or methoxy, n represents a number 0, 1 or 2, Z represents the group (Ia)

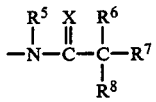

or the group (Ib)

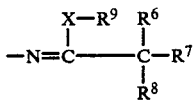

where

X represents oxygen, sulphur, an N—$R^{10}$ or N—O—$R^{11}$ group, where $R^{10}$ and $R^{11}$, independently of one another, represent hydrogen, or alkyl having 1 to 4 carbon atoms, alkenyl or alkinyl having 2 to 4 carbon atoms in each case, $R^5$ represents hydrogen, or alkyl having 1 to 4 carbon atoms, or alkenyl or alkinyl having 2 to 6 carbon atoms in each case, $R^6$ represents hydrogen, fluorine, chlorine, bromine cyano, alkyl, having 1 to 4 carbon atoms, which is optionally mono- or polysubstituted, identically or differently, by fluorine, chlorine and bromine, alkenyl having 2 to 4 carbon atoms, phenyl or benzyl which are in each case optionally mono- to pentasubstituted, identically or differently, by fluorine, chlorine, bromine, trifluoromethyl, methyl and methoxy, or represent the —$OR^{12}$ or $S(O)_m$—$R^{12}$ radicals, where $R^{12}$ represents alkyl, having 1 to 4 carbon atoms, which is optionally mono- or polysubstituted identically or differently, by fluorine, chlorine, bromine, methoxy or ethoxy, or represents phenyl which is optionally mono- to pentasubstituted, identically or differently, by fluorine, chlorine, bromine and $C_1$-$C_4$-alkyl, and m represents a number 0, 1 or 2, $R^7$ and $R^8$, independently of one another, represent fluorine, chlorine, bromine or alkyl, having 1 to 4 carbon atoms, which is optionally mono- or polysubstituted, identically or differently, by fluorine, chlorine and bromine, $R^9$ represents alkyl, having 1 to 4 carbon atoms, which is optionally mono- or polysubstituted, identically or differently, by halogen or $C_1$-$C_4$-alkoxy, or represents alkenyl or alkinyl having 3 or 4 carbon atoms in each case, or $R^6$ and $R^7$ or $R^6$ and $R^8$, together with the neighboring carbon atom, represent a saturated or unsaturated ring, having 3 to 7 ring atoms, which, in addition to carbon, may also contain oxygen or sulphur, and which may be mono- or polysubstituted, identically or differently, by fluorine, chlorine or $C_1$-$C_4$-alkyl, or $R^5$ and $R^7$ or $R^5$ and $R^{10}$ or $R^7$ and $R^9$ or $R^8$ and $R^9$ or $R^7$ and $R^8$ together represent an alkylene chain having 2 to 5 carbon atoms or an alkenylene chain having 2 to 5 carbon atoms, which may in each case be mono- or polysubstituted, identically or differently, by halogen, $C_1$-$C_4$-alkyl or $C_1$-$C_4$-alkoxy, or $R^5$ and $R^{11}$ together represent an alkylene chain having 1 to 4 carbon atoms or an alkenylene chain having 2 to 4 carbon atoms, which may in each case be mono- or polysubstituted, identically or differently, by halogen or $C_1$-$C_4$-alkyl, or X and $R^9$ together represent the

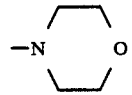

radical.

Particularly preferred compounds of the formula (I) are those in which $R^1$, $R^2$ and $R^3$, independently of one another, represent hydrogen, chlorine, cyano, trifluoromethyl, methyl, ethyl or methoxy, $R^4$ represents fluorine, chlorine, methyl or methoxy, n represents the number 0 or 1, Z represents the group (Ia)

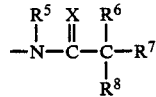

or the group (Ib)

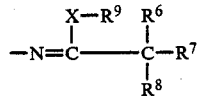

where

X represents oxygen, sulphur, or an N—$R^{10}$ or N—O—$R^{11}$ group, where $R^{10}$ and $R^{11}$, independently of one another, represent hydrogen, or alkyl having 1 to 3 carbon atoms, or alkenyl or alkinyl hving 2 or 3 carbon atoms in each case, $R^5$ represents hydrogen, or alkyl having 1 to 3 carbon atoms, alkenyl having 2 to 4 carbon atoms, or alkinyl having 3 to 4 carbon atoms, $R^6$ represents hydrogen, fluorine, chlorine, bromine, cyano, alkyl having 1 to 4 carbon atoms which is optionally mono- to pentasubstituted, identically or differently, by fluorine and chlorine, phenyl or benzyl which are in each case optionally mono- to trisubstituted, identically or differently, by fluorine, chlorine, trifluoromethyl and methyl, or represents the —$OR^{12}$ or —$S(O)_m$—$R^{12}$ radicals, where $R^{12}$ represents alkyl, having 1 to 4 carbon atoms, which is optionally mono- to pentasubstituted, identically or differently, by fluorine and chlorine, or represents phenyl which is optionally mono to trisubstituted, identically or differently, by fluorine, chlorine and $C_1$-$C_2$alkyl, and m represents a number 0, 1 or 2, $R^7$ and $R^8$, independently of one another, represent fluorine, chlorine or alkyl, having 1 to 2 carbon atoms, which is optionally mono- to pentasubstituted, identically or differently, by fluorine and chlorine, $R^9$ represents alkyl, having 1 or 2 carbon atoms, which is optionally mono- to pentasubstituted, identically or differently, by halogen or $C_1$-$C_4$-alkoxy, or represents alkenyl having 3 or 4 carbon atoms, or $R^6$ and $R^7$ or $R^6$ and $R^8$, together with the neighboring carbon atom, represents a saturated or unsaturated ring, having 3 to 6 ring atoms, which, in addition to carbon, may also contain oxygen and sulphur and which may optionally be mono- to trisubstituted, identically or differently, by fluorine, chlorine, methyl, ethyl, n-propyl and i-propyl, or $R^7$ and $R^8$ together represent an alkylene chain, having 2 to 5 carbon atoms, which may be mono- to pentasubstituted, identically or differently, by fluorine, chlorine, methyl, ethyl or methyoxy, or $R^5$ and $R^7$ or $R^5$ and $R^{10}$ or $R^7$ and $R^9$ or $R^8$ and $R^9$ together represent an alkylene chain, having 2 to 3 carbon atoms, or an alkenylene chain having 3 to 4 carbon atoms, which may in each case be mono- to trisubstituted, identically or differently, by fluorine, chlorine, methyl, ethyl and methoxy, or $R^5$ and $R^{11}$ together represent an alkylene chain, having 1 or 2 carbon atoms, which may be mono- to trisubstituted, identically or differently, by methyl or ethyl.

A group of very particularly preferred pyridylthio-acylanilides of the formula (I) are those in which X represents oxygen and the other substituents have the meaning mentioned above as being particularly preferred.

Another very particularly preferred group are those compounds of the formula (I) in which X represents sulphur and the other substituents have the meaning mentioned above as being particularly preferred.

Very particularly preferred compounds are also those in which X represents N—$R^{10}$ or N—$OR^{11}$, and the remaining substituents have the meaning mentioned above as being particularly preferred.

The pyridylthio-acylanilides of the formula (I) listed in the following Table 1 may be mentioned as examples:

TABLE 1

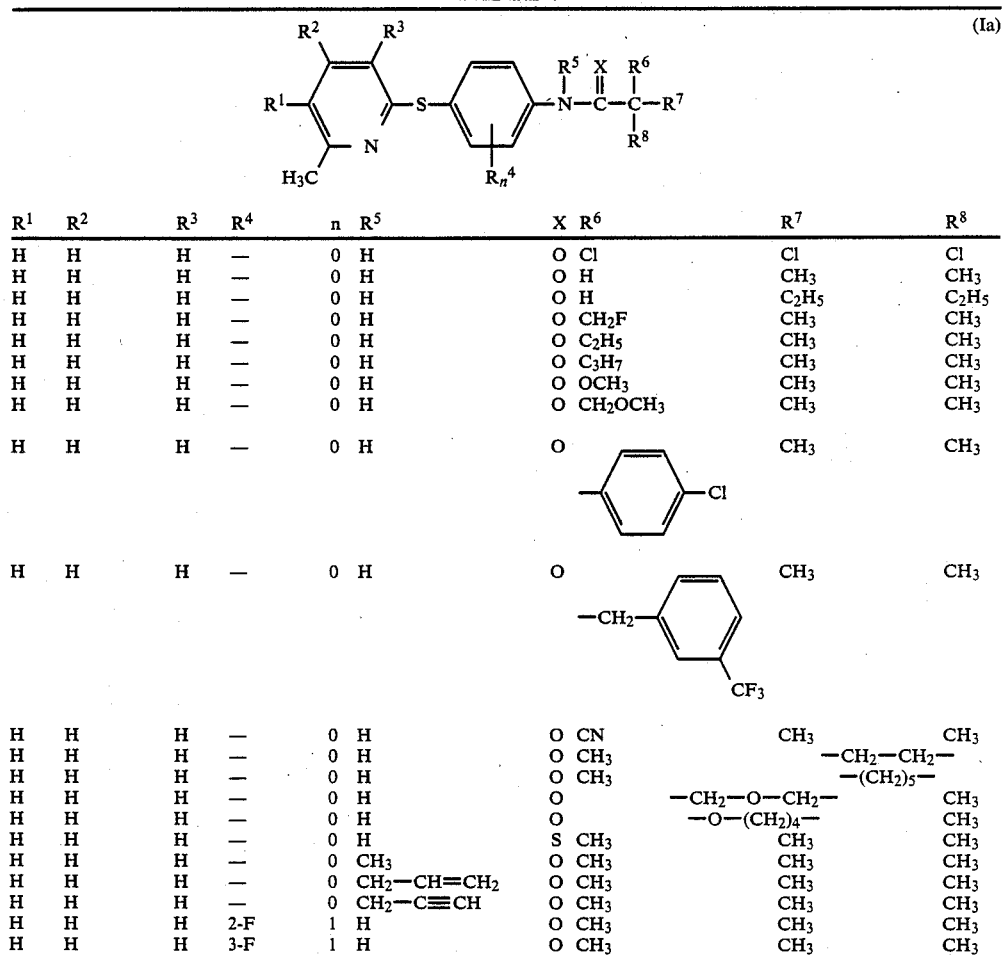

(Ia)

| $R^1$ | $R^2$ | $R^3$ | $R^4$ | n | $R^5$ | X | $R^6$ | $R^7$ | $R^8$ |
|---|---|---|---|---|---|---|---|---|---|
| H | H | H | — | 0 | H | O | Cl | Cl | Cl |
| H | H | H | — | 0 | H | O | H | $CH_3$ | $CH_3$ |
| H | H | H | — | 0 | H | O | H | $C_2H_5$ | $C_2H_5$ |
| H | H | H | — | 0 | H | O | $CH_2F$ | $CH_3$ | $CH_3$ |
| H | H | H | — | 0 | H | O | $C_2H_5$ | $CH_3$ | $CH_3$ |
| H | H | H | — | 0 | H | O | $C_3H_7$ | $CH_3$ | $CH_3$ |
| H | H | H | — | 0 | H | O | $OCH_3$ | $CH_3$ | $CH_3$ |
| H | H | H | — | 0 | H | O | $CH_2OCH_3$ | $CH_3$ | $CH_3$ |
| H | H | H | — | 0 | H | O | —C6H4—Cl (p) | $CH_3$ | $CH_3$ |
| H | H | H | — | 0 | H | O | —$CH_2$—C6H4—$CF_3$ (m) | $CH_3$ | $CH_3$ |
| H | H | H | — | 0 | H | O | CN | $CH_3$ | $CH_3$ |
| H | H | H | — | 0 | H | O | $CH_3$ | —$CH_2$—$CH_2$— | |
| H | H | H | — | 0 | H | O | $CH_3$ | —$(CH_2)_5$— | |
| H | H | H | — | 0 | H | O | | —$CH_2$—O—$CH_2$— | $CH_3$ |
| H | H | H | — | 0 | H | O | | —O—$(CH_2)_4$— | $CH_3$ |
| H | H | H | — | 0 | H | S | $CH_3$ | $CH_3$ | $CH_3$ |
| H | H | H | — | 0 | $CH_3$ | O | $CH_3$ | $CH_3$ | $CH_3$ |
| H | H | H | — | 0 | $CH_2$—CH=$CH_2$ | O | $CH_3$ | $CH_3$ | $CH_3$ |
| H | H | H | — | 0 | $CH_2$—C≡CH | O | $CH_3$ | $CH_3$ | $CH_3$ |
| H | H | H | 2-F | 1 | H | O | $CH_3$ | $CH_3$ | $CH_3$ |
| H | H | H | 3-F | 1 | H | O | $CH_3$ | $CH_3$ | $CH_3$ |

TABLE 1-continued (Ia)

Structure: pyridine with $H_3C$ at 6-position, $R^1$ at 5, $R^2$ at 4, $R^3$ at 3, and S at 2 position connected to a phenyl ring (with $R^4_n$ substituents) which is connected to N($R^5$)—C(=X)—C($R^7$)($R^8$)—$R^6$.

| $R^1$ | $R^2$ | $R^3$ | $R^4$ | n | $R^5$ | X | $R^6$ | $R^7$ | $R^8$ |
|---|---|---|---|---|---|---|---|---|---|
| H | H | H | 2-Cl | 1 | H | O | $CH_3$ | $CH_3$ | $CH_3$ |
| H | H | H | 3-Cl | 1 | H | O | $CH_3$ | $CH_3$ | $CH_3$ |
| H | H | H | 2-Br | 1 | H | O | $CH_3$ | $CH_3$ | $CH_3$ |
| H | H | H | 2-$CH_3$ | 1 | H | O | $CH_3$ | $CH_3$ | $CH_3$ |
| H | H | H | 3-$CH_3$ | 1 | H | O | $CH_3$ | $CH_3$ | $CH_3$ |
| H | H | H | 2-$OCH_3$ | 1 | H | O | $CH_3$ | $CH_3$ | $CH_3$ |
| H | H | H | 3-$OCH_3$ | 1 | H | O | $CH_3$ | $CH_3$ | $CH_3$ |
| H | H | Cl | — | 0 | H | O | $CH_3$ | $CH_3$ | $CH_3$ |
| H | H | F | — | 0 | H | O | $CH_3$ | $CH_3$ | $CH_3$ |
| H | H | CN | — | 0 | H | O | $CH_3$ | $CH_3$ | $CH_3$ |
| H | H | $CH_3$ | — | 0 | H | O | $CH_3$ | $CH_3$ | $CH_3$ |
| H | Cl | H | — | 0 | H | O | $CH_3$ | $CH_3$ | $CH_3$ |
| H | F | H | — | 0 | H | O | $CH_3$ | $CH_3$ | $CH_3$ |
| H | $OCH_3$ | H | — | 0 | H | O | $CH_3$ | $CH_3$ | $CH_3$ |
| H | $SCH_3$ | H | — | 0 | H | O | $CH_3$ | $CH_3$ | $CH_3$ |
| H | $CH_3$ | H | — | 0 | H | O | Cl | Cl | Cl |
| H | $CH_3$ | H | — | 0 | H | O | H | $CH_3$ | $CH_3$ |
| H | $CH_3$ | H | — | 0 | H | O | $CH_2F$ | $CH_3$ | $CH_3$ |
| H | $CH_3$ | H | — | 0 | H | O | —CH=$CH_2$ | $CH_3$ | $CH_3$ |
| H | $CH_3$ | H | — | 0 | H | O | $OCH_3$ | $CH_3$ | $CH_3$ |
| H | $CH_3$ | H | — | 0 | H | O | —$CH_2OCH_3$ | $CH_3$ | $CH_3$ |
| H | $CH_3$ | H | — | 0 | H | O | $SCH_3$ | $CH_3$ | $CH_3$ |
| H | $CH_3$ | H | — | 0 | H | O | —$SO_2CH_3$ | $CH_3$ | $CH_3$ |
| H | $CH_3$ | H | — | 0 | H | O | 4-chlorophenyl | $CH_3$ | $CH_3$ |
| H | $CH_3$ | H | — | 0 | H | O | —$CH_2$-(3-$CF_3$-phenyl) | $CH_3$ | $CH_3$ |
| H | $CH_3$ | H | — | 0 | H | O | $CH_3$ | —$CH_2$—$CH_2$— | |
| H | $CH_3$ | H | — | 0 | H | O | $CH_3$ | —$(CH_2)_4$— | |
| H | $CH_3$ | H | — | 0 | H | O | —$CH_2$—O—$CH_2$— | $CH_3$ | $CH_3$ |
| H | $CH_3$ | H | — | 0 | H | S | $CH_3$ | $CH_3$ | $CH_3$ |
| H | $CH_3$ | H | — | 0 | $CH_3$ | O | $CH_3$ | $CH_3$ | $CH_3$ |
| H | $CH_3$ | H | — | 0 | —$CH_2$—CH=$CH_2$ | O | $CH_3$ | $CH_3$ | $CH_3$ |
| H | $CH_3$ | H | — | 0 | —$CH_2$—C≡CH | O | $CH_3$ | $CH_3$ | $CH_3$ |
| H | $CH_3$ | H | — | 0 | —$CH_2$— | O | $CH_3$ | —$CH_2$— | $CH_3$ |
| H | $CH_3$ | H | — | 0 | —$CH_2$— | O | $CH_3$ | —$CH_2$—$CH_2$— | $CH_3$ |
| H | $CH_3$ | H | — | 0 | $(CH_2)_2$—N | | $CH_3$ | $CH_3$ | $CH_3$ |
| H | $CH_3$ | H | — | 0 | $(CH_2)_3$—N | | $CH_3$ | $CH_3$ | $CH_3$ |
| H | $CH_3$ | H | 2-F | 1 | H | O | $CH_3$ | $CH_3$ | $CH_3$ |
| H | $CH_3$ | H | 3-F | 1 | H | O | $CH_3$ | $CH_3$ | $CH_3$ |
| H | $CH_3$ | H | 2-Cl | 1 | H | O | $CH_3$ | $CH_3$ | $CH_3$ |
| H | $CH_3$ | H | 3-Cl | 1 | H | O | $CH_3$ | $CH_3$ | $CH_3$ |
| H | $CH_3$ | H | 3,5-Cl | 2 | H | O | $CH_3$ | $CH_3$ | $CH_3$ |
| H | $CH_3$ | H | 2-Br | 1 | H | O | $CH_3$ | $CH_3$ | $CH_3$ |
| H | $CH_3$ | H | 2-$CH_3$ | 1 | H | O | $CH_3$ | $CH_3$ | $CH_3$ |
| H | $CH_3$ | H | 3-$CH_3$ | 1 | H | O | $CH_3$ | $CH_3$ | $CH_3$ |
| H | $CH_3$ | H | 3-$OCH_3$ | 1 | H | O | $CH_3$ | $CH_3$ | $CH_3$ |
| H | $CH_3$ | H | 3-$OCH_3$ | 1 | H | O | $CH_3$ | $CH_3$ | $CH_3$ |
| H | $CH_3$ | F | — | 0 | H | O | $CH_3$ | $CH_3$ | $CH_3$ |
| H | $CH_3$ | Cl | — | 0 | H | O | $CH_3$ | $CH_3$ | $CH_3$ |
| H | $CH_3$ | $CH_3$ | — | 0 | H | O | $CH_3$ | $CH_3$ | $CH_3$ |
| H | $CF_3$ | H | — | 0 | H | O | $CH_3$ | $CH_3$ | $CH_3$ |
| H | $C_2H_5$ | H | — | 0 | H | O | $CH_3$ | $CH_3$ | $CH_3$ |
| H | $C_3H_7$ | H | — | 0 | H | O | $CH_3$ | $CH_3$ | $CH_3$ |
| H | $CH(CH_3)_2$ | H | — | 0 | H | O | $CH_3$ | $CH_3$ | $CH_3$ |
| F | H | H | — | 0 | H | O | $CH_3$ | $CH_3$ | $CH_3$ |
| Cl | $CH_3$ | H | — | 0 | H | O | $CH_3$ | $CH_3$ | $CH_3$ |
| $CH_3$ | $CH_3$ | H | — | 0 | H | O | $CH_3$ | $CH_3$ | $CH_3$ |

TABLE 2

(Ib)

Structure: pyridyl-thio-phenyl-N=C(R⁶)(R⁷)(R⁸)-X-R⁹ with substituents R¹, R², R³ on pyridine and R⁴ on phenyl

| R¹ | R² | R³ | R⁴ | n | X | R⁶ | R⁷ | R⁸ | R⁹ |
|----|----|----|----|---|---|----|----|----|----|
| H | H | H | — | 0 | O | CH$_3$ | CH$_3$ | CH$_3$ | CH$_3$ |
| H | H | H | — | 0 | O | CH$_3$ | CH$_3$ | | —CH$_2$—CH$_2$ |
| H | H | H | — | 0 | O | CH$_3$ | CH$_3$ | | —(CH$_2$)$_3$— |
| H | H | CH$_3$ | — | 0 | S | CH$_3$ | CH$_3$ | CH$_3$ | CH$_3$ |
| H | H | CH$_3$ | — | 0 | S | CH$_3$ | CH$_3$ | CH$_3$ | —CH$_2$—CH=CH$_2$ |
| H | H | CH$_3$ | — | 0 | S | CH$_3$ | CH$_3$ | CH$_3$ | —CH$_2$—C≡CH |
| H | H | CH$_3$ | — | 0 | S | CH$_3$ | CH$_3$ | | —CH$_2$—CH$_2$— |
| H | H | CH$_3$ | — | 0 | CH$_3$—N | CH$_3$ | CH$_3$ | CH$_3$ | CH$_3$ |
| H | H | CH$_3$ | — | 0 | CH$_3$—N | CH$_3$ | CH$_3$ | CH$_3$ | CH$_2$—CH=CH$_2$ |
| H | H | CH$_3$ | — | 0 | CH$_2$—CH$_2$—N | CH$_3$ | CH$_3$ | CH$_3$ | O—CH$_2$—CH$_2$ |

If 4-(4,6-dimethyl-pyridyl-2-thio)-aniline and pivaloyl chloride are used as starting compounds, then the course of the process (a) according to the invention may be represented by the following equation:

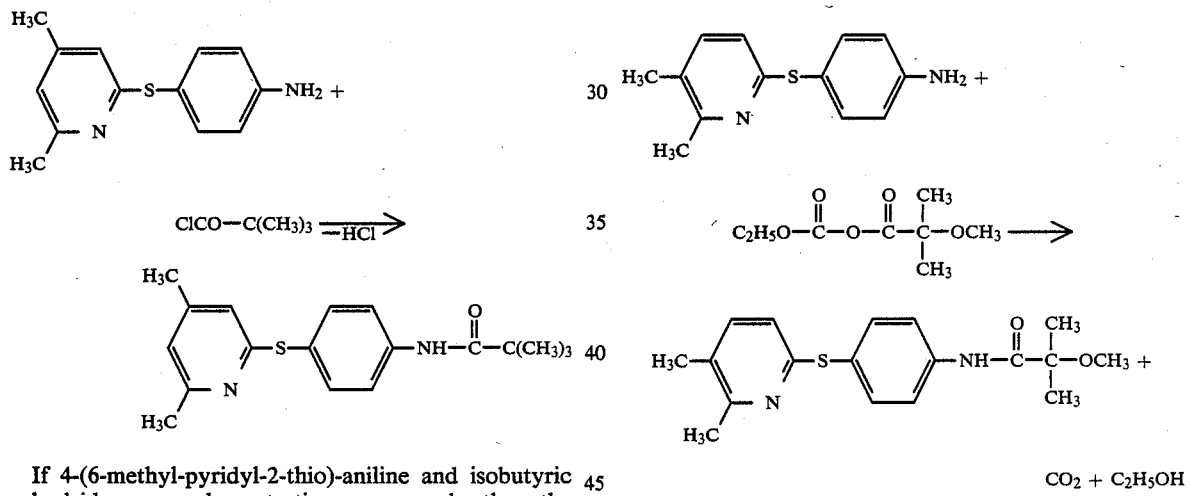

If 4-(6-methyl-pyridyl-2-thio)-aniline and isobutyric anhydride are used as starting compounds, then the course of the process (a) according to the invention may be represented by the following equation:

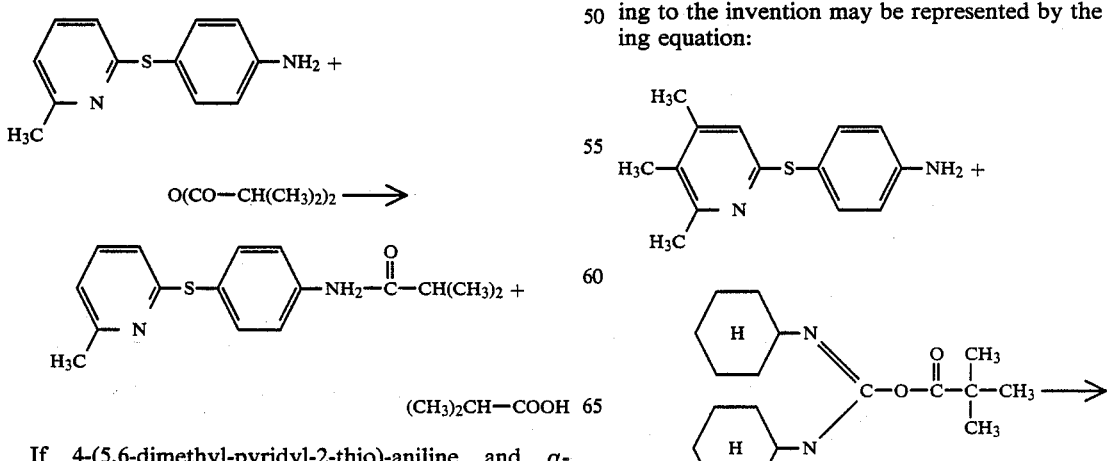

If 4-(5,6-dimethyl-pyridyl-2-thio)-aniline and α-methoxy-isobutyric ethoxycarbonic anhydride are used as starting compounds, then the course of the process (a) according to the invention may be represented by the following equation:

If 4-(4,5,6-trimethyl-pyridyl-2-thio)-aniline and O-pivaloyloxy-dicyclohexyl-isourea are used as starting compounds, then the course of the process (a) according to the invention may be represented by the following equation:

-continued

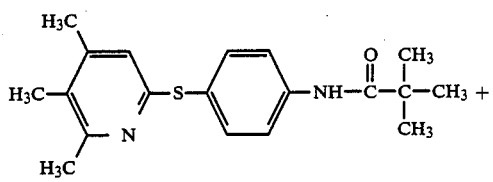

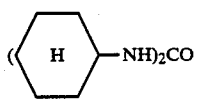

If 2-chloro-4,6-dimethyl-pyridine and 4-pivaloylaminothiophenol are used as starting compounds, then the course of the process (b) according to the invention may be represented by the following equation:

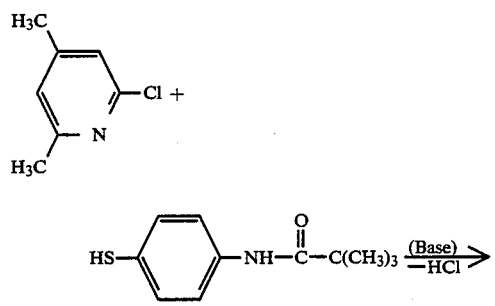

-continued

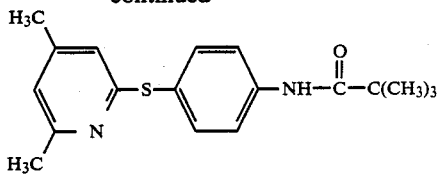

If 4=-(4,6-dimethyl-pyridyl-2-thio)-pivalanilide and allyl bromide are used as starting compounds, then the course of the process (c) according to the invention may be represented by the following equation:

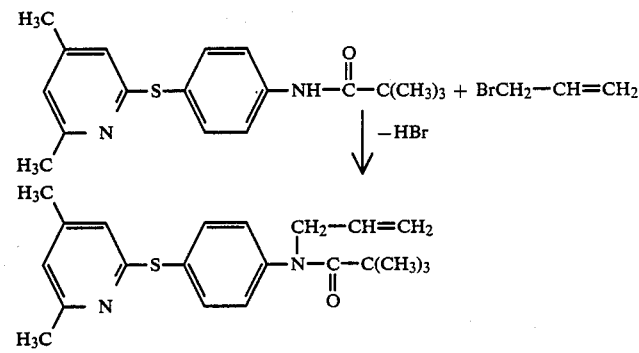

If 4'-(4,6-dimethyl-pyridyl-2-thio)-thiopivalanilide and methyl iodide are used as starting compounds, then the course of the process (c) according to the invention may be represented by the following equation:

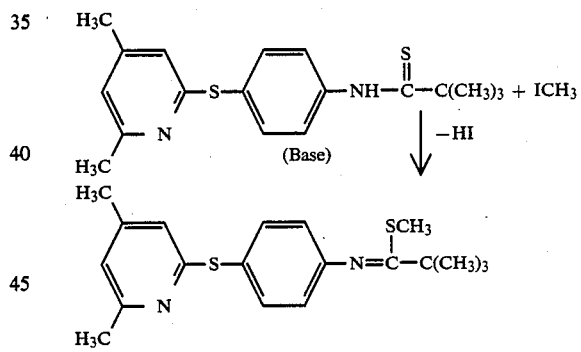

If pivaloyl-4-(4,6-dimethyl-pyridyl-2-thio)-phenyl imide chloride and methanol or methanethiol or dimethylamine are used as starting compounds, then the course of the process (d) according to the invention may be represented by the following equation:

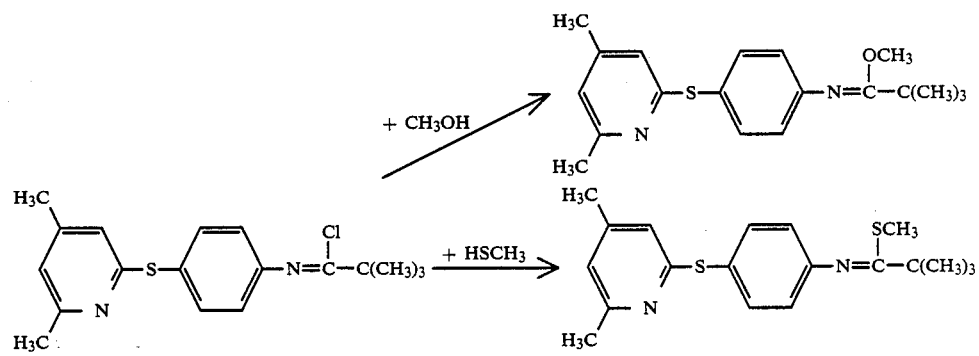

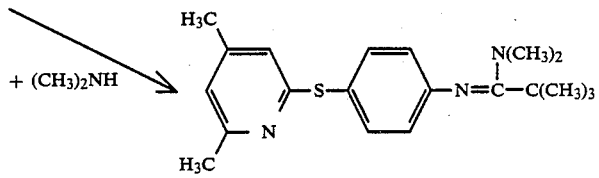

If 4'-(4,6-dimethyl-pyridyl-2-thio)-pivalanilide and phosphorus-V sulphide are used as starting compounds, then the course of the process (e) according to the invention may be represented by the following equation:

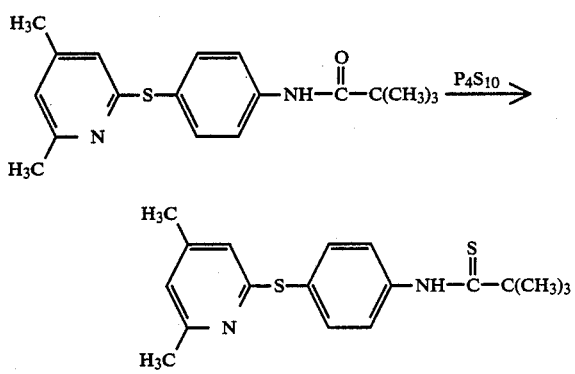

The aniline derivatives required as starting compounds in the process (a) according to the invention are generally defined by the formula (II). In this formula, $R^1$, $R^2$, $R^3$, $R^4$, $R^5$ and n preferably have those meanings which have already been mentioned in connection with the description of the substances of the formula (I) according to the invention as being preferred for these radicals or for this index.

The aniline derivatives of the formula (II) are hitherto not known. They can be prepared by (A) reacting pyridine derivatives of the formula (IV)

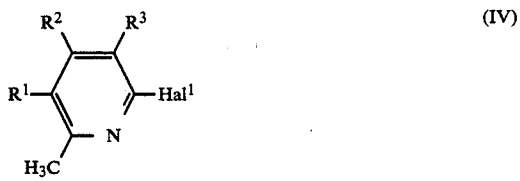

in which $R^1$, $R^2$, $R^3$, and $Hal^1$ have the abovementioned meaning,
with 4-amino-thiophenols of the formula (IX),

in which $R^4$, $R^5$ and n have the abovementioned meaning,
in the presence of an acid acceptor and if appropriate in the presence of a diluent, or (B) reducing 2-(4-nitro-phenylthio)-pyridine derivatives of the formula (X),

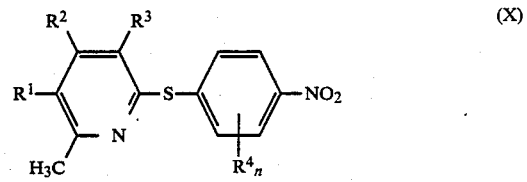

in which $R^1$, $R^2$, $R^3$, $R^4$ and n have the abovementioned meaning,
by conventional methods, if appropriate in the presence of a diluent.

The pyridine derivatives required as starting compounds in the process (A) above are defined by the formula (IV). In this formula, $R^1$, $R^2$ and $R^3$ preferably have those meanings which have already been mentioned in connection with the description of the substances of the formula (I) according to the invention as being preferred for these radicals. $Hal^1$ preferably represents fluorine, chlorine or bromine.

The following may be mentioned as examples of pyridine derivatives of the formula (IV):
2-chloro-6-methyl-pyridine
2-bromo-6-methyl-pyridine
2,3-dichloro-6-methyl-pyridine
2,4-dichloro-6-methyl-pyridine
2-chloro-5-fluoro-6-methyl-pyridine
2-chloro-4-methoxy-6-methyl-pyridine
2-chloro-4-methylmercapto-6-methyl-pyridine
2-chloro-3-cyano-6-methyl-pyridine
2-chloro-3,6-dimethyl-pyridine
2-chloro-4,6-dimethyl-pyridine
2-fluoro-4,6-dimethyl-pyridine
2-chloro-6-methyl-4-propyl-pyridine
2-chloro-6-methyl-4-isopropyl-pyridine
2-chloro-6-methyl-4-trifluoromethyl-pyridine
2,3-dichloro-4,6-dimethyl-pyridine
2-chloro-5-fluoro-4,6-dimethyl-pyridine
2-chloro-3-cyano-4,6-dimethyl-pyridine
2-chloro-3,4,6-trimethyl-pyridine
2-chloro-4,5,6-trimethyl-pyridine The pyridine derivatives of the formula (IV) are known or can be prepared in a simple manner by methods which are known in the principle. Thus, pyridine derivatives of the formula (IV) are obtained, for example, by reacting 2-hydroxy-pyridine derivatives (dihydro-pyrid-2-one derivatives) with inorganic acid halides, such as, for example, phosphoroxy chloride or phosphorus pentachloride, or alternatively by reacting the corresponding 2-aminopyridine derivative with nitrous acid in the presence of hydrohalic acids.

The 4-amino-thiophenols furthermore required as starting compounds in the process (A) are defined by the formula (IX). In this formula, $R^4$, $R^5$ and n preferably have those meanings which have already been mentioned in connection with the description of the substances of the formula (I) according to the invention as being preferred for these radicals or for this index.

The following may be mentioned as examples of 4-amino-thiophenols of the formula (IX):
4-amino-thiophenol
4-methylamino-thiophenol
2-fluoro-4-amino-thiophenol
3-fluoro-4-amino-thiophenol
2-chloro-4-amino-thiophenol
3-chloro-4-amino-thiophenol
2,6-dichloro-4-amino-thiophenol
2-methyl-4-amino-thiophenol
3-methyl-4-amino-thiophenol
2-methoxy-4-amino-thiophenol
3-methoxy-4-amino-thiophenol The 4-amino-thiophenols of the formula (IX) are known or can be prepared in a simple fashion by methods which are known in principle.

All acid acceptors which can conventionally be used for such reactions can be used as acid acceptors when carrying out the process (A). Alkali metal and alkaline earth metal oxides, hydroxides and carbonates, such as sodium hydroxide, potassium hydroxide, calcium hydroxide, sodium carbonate and potassium carbonate, furthermore alkali metal alcoholates, amides and hydrides, such as, for example, sodium methylate, sodium ethylate, potassium tert.-butylate, sodium amide and sodium hydride may preferably be used.

All conventional inert organic solvents may be used as diluents when carrying out the process (A). Preferably suitable are hydrocarbons, such as benzine, toluene and xylene, furthermore ethers, such as dioxane, glycol dimethyl ether and diglycol dimethyl ether, in addition nitriles, such as acetonitrile, and also strongly polar solvents, such as dimethyl sulphoxide, sulpholane and dimethylformamide.

The reaction temperatures may be varied within a relatively wide range when carrying out the process (A). In general, the process is carried out at temperatures between 0° C. and 200° C., preferably between 50° C. and 150° C.

The reaction according to the process (A) is generally carried out under atmospheric pressure.

When carrying out the process (A), the starting compounds of the formulae (IV) and (IX) are generally reacted in approximately equimolar amounts. However, it is also possible to use one of the components in excess. Working-up is effected by conventional methods.

The 2-(4-nitro-phenylthio)-pyridine derivatives required as starting compounds in the process (B) are defined by the formula (X). In this formula $R^1$, $R^2$, $R^3$, $R^4$ and n preferably have those meanings which have already been mentioned in connection with the description of the substances of the formula (I) according to the invention as being preferred for these radicals or for this index.

The compounds of the formula (X) are known or can be prepared in a simple fashion by methods which are known in principle. Thus, compounds of the formula (X) are obtained, for example, by reacting pyridine derivatives of the formula (IV),

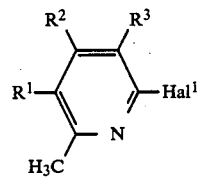
(IV)

in which $R^1$, $R^2$, $R^3$ and $Hal^1$ have the abovementioned meaning,
with 4-nitro-thiphenols of the formula (XI),

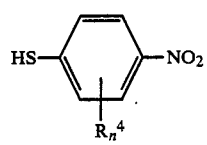
(XI)

in which $R^4$ and n have the abovementioned meaning, in the presence of an acid acceptor and if appropriate in the presence of a diluent at temperatures between 0° C. and 200° C., preferably between 50° C. and 150° C. Suitable acid acceptors and diluents here are preferably those substances which have already been mentioned in connection with the process (A) as being acid acceptors and solvents which may preferably be used.

The compounds of the formula (X) required as intermediates are obtained by a further process by reacting 2-mercapto-pyridines of the formula (XII)

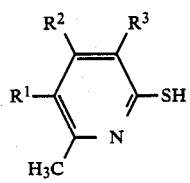
(XII)

in which $R^1$, $R^2$ and $R^3$ have the abovementioned meaning, wih 4-halogen-nitro-benzenes of the formula (XIII),

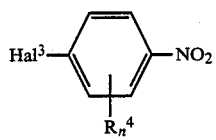
(XIII)

in which $R^4$ and n have the abovementioned meaning and $Hal^3$ represents fluorine, chlorine or bromine, in the presence of an acid acceptor and if appropriate in the presence of a diluent at temperatures between 0° C. and 200°, preferably between 50° C. and 150° C. Suitable acid acceptors and diluents here are preferably those substances which have already been mentioned in a corresponding fashion in connection with the process (A).

Suitable reducing agents in the process (B) are all those substances which are conventionally employed for reducing aromatic nitro compounds. Metals in elemental form, such as iron, zinc and tin, furthermore metal compounds in low valency states, such as iron-(II) and tin-(II) salts, and, in addition, non-metal compounds in low valence states, such as, for exaample, salts of hydrogen sulphide, alkali metal sulphites and alkali metal dithionites, may preferably be used. In addition, the reduction can also be carried out by catalytic hydrogenation using hydrogen in the presence of a catalyst, such as, for example, Raney nickel.

Suitable diluents in the process (B) are all organic solvents which are conventionally suitable for such reductions. The reaction temperatures may be varied within a relatively wide range. They correspond to the temperatures which are used in analogous reactions.

The reduction by the process (B) and the workingup of the resultant reaction mixture are carried out by conventional methods.

The carboxylic acids and derivatives thereof furthermore required as reaction components in the process (a) according to the invention are clearly defined by the formula (III). In this formula, $R^6$, $R^7$, $R^8$ and X preferably have those meanings which have already been mentioned in connection with the description of the substances of the formula (I) according to the invention as being preferred for these radicals. Y preferably represents hydroxyl, fluorine, chlorine, bromine, acyloxy, $C_1$–$C_4$-alkoxycarbonyloxy, phenyl- or p-tolyloxycarbonyloxy, methyl- or ethylsulphonyloxy or phenyl- or p-tolylsulphonyloxy, or for the

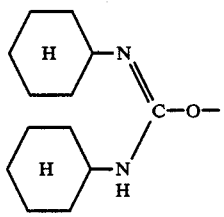

group.

The following may be mentioned as examples of compounds of the formula (III):
trichloroacetic acid
trifluoroacetic acid
α,α-dichloropropionic acid
isobutyric acid
α-chloro-isobutyric acid
α-bromo-isobutyric acid
α-methoxy-isobutyric acid
α-phenoxy-isobutyric acid
α-(4-chloro-phenoxy)-isobutyric acid
α-(2-methyl-4-chloro-phenoxy)-isobytyric acid
α-methylmercapto-isobutyric acid
α-methylsulphonyl-isobutyric acid
α-methyl-butyric acid
pivalic acid
β-fluoro-pivalic acid
β-chloro-pivalic acid
β,β'-difluoro-pivalic acid
β,β'-dichloro-pivalic acid
β,β',β''-trifluoro-pivalic acid
β,β',β''-trichloro-pivalic acid
α,α-dimethyl-butyric acid
α-vinyl-isubutyric acid
α-ethinyl-isobutyric acid
α,α-dimethyl-valeric acid
α-methyl-α-ethyl-butyric acid
α,α-dimethyl-phenylacetic acid
α,α-dimethyl-(4-chloro-phenyl)-acetic acid
α,α-dimethyl-(3,4-dichloro-phenyl)-acetic acid
α,α-dimethyl-3-trifluoromethyl-phenyl)-acetic acid
α-benzyl-isobutyric acid
α-(4-chloro-benzyl)-isobutyric acid
α-(4-methoxy-benzyl)-isobutyric acid
α,α-dimethyl-cyanoacetic acid
cyclopropane-carboxylic acid
1-methyl-cyclopropane-carboxylic acid
2,2-dichloro-1-methyl-cyclopropane-carboxylic acid
cyclopentane-carboxylic acid
1-methyl-cyclopentane-carboxylic acid
cyclohexane-carboxylic acid
1-methyl-cyclohexane-carboxylic acid
1-methyl-4-isopropyl-cyclohexane-carboxylic acid
3-methyl-oxetane-3-carboxylic acid
2-methyl-furfuryl-2-carboxylic acid
2-methyl-tetrahydropropane-2-carboxylic acid The carboxylic acid derivatives of the formula (III) are known or can be prepared in a simple fashion by methods which are known in principle.

Thus, for example, asymmetrical carboxylic acid anhydrides of the compounds of the formula (III) are obtained when carboxylic acids (i.e. Y=hydroxyl in the formula (III)) are reacted with alkyl or aryl carbonate chlorides (alkyl—O—CO—Cl or aryl—O—CO—Cl) or with alkyl-or arylsulphonyl chlorides in the presence of a diluent, such as, for example, methylene chloride, and in the presence of an acid acceptor, such as, for example, triethylamine or pyridine, at temperatures between −20° C. and +100° C., preferably between 0° C. and 50° C.

The asymmetrical acid anhydrides of the formula (III) are generally not isolated in pure form, but are further used in the form produced, if appropriate after prior removal of diluent, and/or as salts.

If the corresponding carboxylic acid halides are used, then suitable acid acceptors in the reaction according to the process (a) according to the invention are all conventional acid acceptors. Tertiary amines, such as triethylamine, pyridine, and N,N-dimethyl-aniline, furthermore alkaline earth metal oxides, such as magnesium and calcium oxide, in addition alkali metal and alkaline earth metal carbonates, such as sodium carbonate, potassiumc carbonate and calcium carbonate, may preferably be used. It is also possible to use the respective aniline derivatives of the formula (II) simultaneously as acid acceptors. To this purpose, the aniline compound concerned must be employed in at least an amount such that the hydrogen halide being liberated can be bound.

When using the acid halides, all solvents which are inert towards these compounds may be employed as diluents in the process (a) according to the invention. Hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, in addition ketones, such as acetone and methyl isopropyl ketone, moreover ethers, such as diethyl ether, tetrahydrofuran and dioxane, additionally carboxylic acid esters, such as ethyl acetate, and also strongly polar solvents, such as dimethyl sulphoxide and sulpholane, may preferably be used. If the stability of the acid halide to hydrolysis permits, the reaction can also be carried out in the presence of water.

When using the acid halides as carboxylic acid derivatives of the formula (III), the reaction temperatures may be varied within a relatively wide range when carrying out the process (a) according to the invention. If the process is carried out without solvent and acid acceptor, then a procedure is generally followed in which the components are initially allowed to react at temperatures between −20° C. and +20° C., and then heated to temperatures between 70° C. and 200° C. If the process is carried out in the presence of a diluent and an acid acceptor, the reaction temperatures are generally between −20° C. and +100° C., preferably between 0° C. and 50° C.

The process (a) according to the invention is generally carried out under atmospheric pressure.

When carrying out the process (a) according to the invention, the starting compounds of the formula (II) and the appropriate acid halide of the formula (III) are generally used in approximately equimolar amounts. However, it is also possible to employ either component in an excess (up to 2 moles). The working-up is then effected by conventional methods. In general, a procedure is followed in which the precipitated salts are removed and the reaction mixture remaining is concentrated by stripping the diluent. If the process is carried out in the presence of water or water-miscible solvents, then a procedure can also be followed in which the reaction mixture is diluted with water, the resulting mixture is filtered under suction or extracted with an organic solvent which is sparingly miscible with water, the organic phase is washed and concentrated, and the residue remaining is subjected, if appropriate, to conventional purification processes.

If symmetrical or asymmetrical carboxylic acid anhydrides are used as reaction components of the formula (III) in the process (a) according to the invention, then those diluents which are also preferably suitable when using acid halides may preferably be used as diluents. In addition, a carboxylic acid anhydride employed in excess can also function as diluent.

The reaction temperatures may also be varied within a relatively wide range when using carboxylic acid anhydrides in the process (a) according to the invention. In general, the process is carried out at temperatures between −20° C. and +150° C., preferably between 0° C. and 100° C.

When carrying out the process (a) according to the invention, the starting compounds of the formula (II) and the carboxylic acid anhydride of the formula (III) are generally used in approximately equivalent amounts. However, it is also possible to employ the carboxylic acid anhydride in an excess (up to 5 moles). The working-up is effected by conventional methods. In general, a procedure is followed in which the diluent and the carboxylic acid anhydride present in excess, and also the carboxylic acid produced, are removed by distillation or by washing with an organic solvent or with water.

The reaction with those carboxylic acid derivatives of the formula (III) in which Y represents alkylsulphonyloxy, arylsulphonyloxy or the

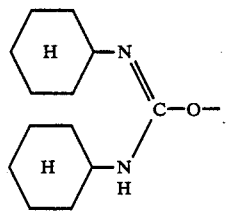

group is also carried out in an analogous fashion to that described for the use of carboxylic acid anhydrides as reaction components of the formula (III).

The pyridine derivatives of the formula (IV) required as starting compounds in the process (b) according to the invention have already been dealt with in connection with the description of the process (A).

The acylaniline derivatives furthermore required as starting compounds in the process (b) accoding to the invention are clearly defined by the formulae (Va) and (Vb). In these formulae, $R^4$, $R^5$, $R^6$, $R^7$, $R^8$, X and n preferably have those meanings which have already been mentioned in connection with the description of the substances of the formula (I) as being preferred for these radicals or for this index.

The compounds of the formuale (Va) and (Vb) are known or can be prepared in a simple manner by methods which are known in principle. Thus, acylaniline derivatives of the formula (Va) are obtained, for example, by reacting 4-amino-thiophenols of the formula

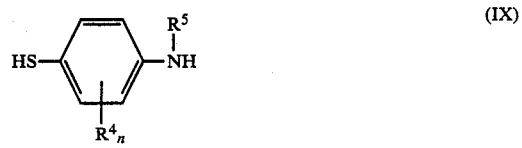

in which $R^4$, $R^5$ and n have the abovementioned meaning, with carboxylic acid derivatives of the formula

in which $R^6$, $R^7$, $R^8$, X and Y have the abovementioned meaning, if appropriate in the presence of a diluent and if appropriate in the presence of an acid acceptor. The reaction conditions here correspond to those which are also used when carrying out the process (a).

All conventional acid acceptors can be employed as acid acceptors when carrying out the process (b) according to the invention. Alkali metal and alkaline earth metal oxides, hydroxides and carbonates, such as sodium hydroxide, potassium hydroxide, magnesium oxide, calcium oxide, sodium carbonate, potassium carbonate and calcium carbonate, furthermore alkali metal and alkaline earth metal amides and hydrides, such as sodium amide, sodium hydride and calcium hydride, and, in addition, also alkali metal alcoholates, such as sodium methylate, sodium ethylate and potassium tert.-butylate may preferably be used.

All conventional inert organic solvents may be employed as diluents in the process (b) according to the invention. Hydrocarbons, such as toluene and xylene, furthermore ethers, such as dibutyl ether, tetrahydrofuran, dioxane, glycol dimethyl ether and diglycol dimethyl ether, in addition nitriles, such as acetonitrile and propionitrile, and moreover polar solvents such as nitrobenzene, dimethyl sulphoxide, sulpholane, dimethylformamide and N-methyl-pyrrolidone, may preferably be used.

The reaction temperatures may be varied within a relatively wide range when carrying out the process (b)

according to the invention. In general, the process is carried out at temperatures between 0° C. and 200° C., preferably between 50° C. and 150° C.

The process (b) according to the invention is generally carried out under atmospheric pressure.

When carrying out the process (b) according to the invention, the reaction components of the formulae (IV) and (Va) or (Vb) are generally employed in approximately equimolar amounts. However, it is also possible to employ either component in an excess (up to 2 moles). In addition, an equimolar amount of acid-binding agent is generally also employed. However, it can also be advantageous to add the acid acceptor in an excess of up to one mole. In detail, a procedure is generally followed in which the acid-binding agent is added to a mixture of the reaction components in a suitable diluent. However, a procedure can also be followed in which, initially, a salt is formed from the acylaniline derivative of the formula (Va) or (Vb) and the acid acceptor and this salt is then reacted with a pyridine derivative of the formula (IV). Furthermore, it is also possible, initially, to separately prepare a salt from the acylaniline derivative of the formula (Va) or (Vb) with an acid acceptor, then to isolate this salt, and subsequently to react it with a pyridine derivative of the formula (IV) in the presence of a suitable diluent, without further addition of an acid acceptor. In each case, working-up is effected by conventional methods.

The carboxyanilides of the formula (I), in which $R^5$ represents hydrogen, required as starting compounds in the process (c) according to the invention are compounds according to the invention and can be obtained by process (a), (b), (c) or (d). In this formula, $R^1$, $R^2$, $R^3$, $R^4$, $R^6$, $R^7$, $R^8$, n and X preferably have the meaning described above.

The aklylating agents furthermore required as starting compounds in the process (c) according to the invention are defined by the formula (VI). In this formula, $R^5$ has the abovementioned meaning. Y preferably represents fluorine, chlorine, methyl- or ethyl-sulphonyloxy, or phenyl- or p-tolysulphonyloxy. The alkylating agents of the formula (VI) are known.

Depending on the type of the substituent X, the reaction between the reaction components in the process (c) takes a different course. If X represents an oxygen atom, then the radical $R^5$ is preferably incorporated at the N atom of the carboxamide group with formation of compounds of the type (Ia). If X denotes a sulphur atom, then the radical $R^5$ (then corresponding to $R^9$) is incorporated on the sulphur atom of the thioamide group with formation of compounds of the type (Ib).

The reactions according to the process (c) are preferably carried out in diluents. Suitable as such are aliphatic and aromatic hydrocarbons, such as hexane or toluene, ethers, such as diethyl ether, tetrahydrofuran or dioxane, acetonitrile or dimethyl sulphoxide, inter alia, and, when thioamides are used, also alcohols, such as methanol and ethanol.

In addition, the reactions according to process (c) are preferably carried out in the presence of an acid-binding base. Suitable as such are: alkali metal and alkaline earth metal oxides, hydroxides and carbonates, and alkali metal alcoholates, amides or hydrides, The reaction components and the acid-binding agent are preferably employed in a stoichiometric ratio to one another, but the acid-binding agent and the reaction component of the formula (VI) may also be employed in an excess of up to one further mole. The reaction temperatures are generally $-50°$ C. to $+200°$ C., preferably 0° C. to 100°.

The carboxylic acid imide halides required as starting compounds in the process (d) according to the invention are defined by the formula (VII). In this formula, $R^1$, $R^2$, $R^3$, $R^4$, $R^6$, $R^7$, $R^8$ and n preferably have the meaning mentioned in the description of the substances of the formula (I) according to the invention as being preferred for these radicals, and $Hal^2$ represents chlorine or bromine. The carboxylic acid imide halides of the formula (VII) are hitherto not known. They are obtained from the pyrdylthioacylanilides of the formula (I), in which $R^5$ represents hydrogen and X represents oxygen, according to the invention by reacting these with inorganic acid chlorides, such as phosphorus-(V) chloride, phosphoroxy chloride, thionyl chloride, phospgene or dihalogeno-phosphanes.

The nucleophiles furthermore required as starting compounds in the process (d) according to the invention are defined by the formula (VIII), in which X denotes an oxygen or sulphur atom or the N—$R^{10}$ or N—O—$R^{11}$ radical, with the same meaning for $R^9$, $R^{10}$ and $R^{11}$ as given above. Accordingly, they are alcohols, mercaptans, ammonia, primary and secondary amines, and also hydroxylamine or its derivatives correspondingly substituted on the N or O atom. These compounds are known from the literature.

The reaction according to process (d) is preferably carried out in diluents and in the presence of an acid-binding agent.

Suitable diluents are: hydrocarbons and halogenated hydrocarbons such as dichloromethane, chloroform or toluene, or ethers, such as diethyl ether, tetrahydrofuran or dioxane. In the case of alcohols as reaction components, these may also be used, in excess, as diluents.

Suitable acid-binding agents are: alkali metal and alkaline earth metal oxides, hydroxides and carbonates, and also tertiary amines, such as triethylamine and pyridine. In the case of ammonia or primary or secondary amines as reaction components, a further mole of these may also be used as acid-binding agent. Such acid-binding agents, in excess, can also function simultaneously as solvents.

The reaction components and the acid-binding agent are preferably employed in an equimolar ratio in process (d), but the nucleophilic reaction component and the acidbinding agent can be employed in an excess of up to several (preferably 5) moles.

The reaction temperatures may be varied within a relatively wide range in process (d). In general, the process is carried out at temperatures between $-50°$ and $+200°$ C., preferably between 0° C. and 100° C.

The carboxanilides required as starting compounds in the process (e) according to the invention are defined by formula (Ic). In this formula, the substituents $R^1$, $R^2$, $R^3$, $R^4$, $R^5$, $R^6$, $R^7$, $R^8$ and n preferably have the meaning preferably given for these substituents in the descriptio of the substances of the formula (I) according to the invention, and X represents an oxygen atom. The compounds of the formula (Ic) are compounds according to the invention, i.e. they are covered by the present invention and can be prepared by the processes described above.

According to the process (e) according to the invention, the compounds of the formula (Ic) where X=oxygen are coverted to compounds of the formula (I) where X=sulphur. Reactions of this type are known in principle. These are carried out by allowing sulphurizing reagents such as $P_4S_{10}$ or 2,4-bis-(4-methoxyphenyl)-2,4-dithiono1,3,2,4-dithiaphosphetane (Lawesson reagent) to act on the compounds of the formula (Ic). The reaction according to process (e) is preferably carried out in the presence of a diluent. Suitable diluents are inert organic solvents. Preferably toluene, xylene and benzene are used.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, arachis, Brassica, Lactuca, Cucumis and Cucurbita.

Monocotyledon weeds of the genera: Echninochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations oil palm plantations, cocoa plantations, soft fruit plantings and hopfields, and for the selective combating of weeds in annual cultures.

The active compounds according to the invention are especially well suited for the selective combating of monocotyledon and dicotyledon weeds in monocotyledon crops, such as, for example, maize and cereals.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl napthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for exampale crushed and fractionated natural rocks such as calcite, marble, pumice, sepiolite and dolomite, as well as synthetic granules of inorganic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5(4H)-one, 4-amino-6-(1,1-dimethyl-ethyl)-3-ethylthio-1,2,4-triazin-5(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5(4H)-one, 2-chloro-4-ethylamino-6-isopropyl-amino-1,3,5-triazine, the R-enantiomer of (trimethylsilyl)- methyl 2-[4-(3,5-dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichlorophenoxy)-propionic acid, 4-chloro-2-methylphenoxy-acetic acid, 2-(2-methyl-4-chloro-phenoxy)-propionic acid, 3,5-diiodo-4-hydroxy-benzonitrile, 3,5-dibromo-4-hydroxy-benzonitrile and diphenyl ethers and phenylpyridazines, such as, for example, pyridates. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentialy on the nature of the desired effect. In general, the amounts used are between 0.01 aand 10 kg of active compound per hectare of soil surface, preferably between 0.05 and 5 kg per ha.

The preparation and use of the active compounds according to the invention can be seen from the following examples.

PREPARATION EXAMPLES

Example 1

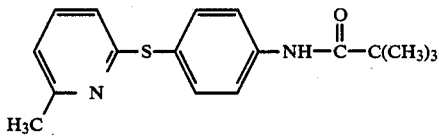

Process (a)

21.6 g (0.1 mol) of 4-(6-methyl-pyridyl-2-thio)-aniline and 10.1 g (0.1 mol) of triethylamine are dissolved in 150 ml of tetrahydrofuran. 12.05 g (0.1 mol) of pivaloyl chloride are added dropwise to this solution at 10° C. to 15° C. The mixture is stirred for 2 hours at room temperature and subsequently poured into 1 l of water. The crystals which separate are filtered off under suction and dried in air.

26.1 g (87% of theory) of 4'-(6-methyl-pyridyl-2-thio)-pivalanilide of melting point 170° C. to 171° C. (recrystallized from toluene) are obtained.

Example 2

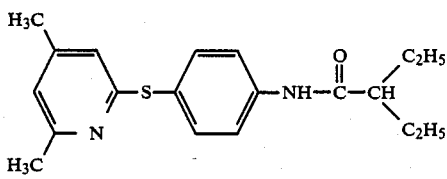

Process (a)

23.0 g (0.1 mol) of 4-(4,6-dimethyl-pyridyl-2-thio)-aniline are refluxed for 5 hours with 23.0 g (0.2 mol) of α-ethyl-butyric anhydride. The mixture is evaporated in vacuo, and the residue is stirred into 1 l of water. The crystals which separate are filtered off under suction and dried in air.

26.9 g (82% of theory) of 4'-(4,6-dimethyl-pridyl-2-thio)-pentane-3-carboxanilide of melting point 152° C. to 154° C. (recrystallized from washing benzine) are obtained.

Example 3

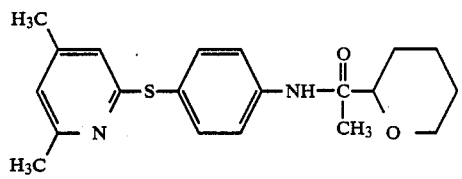

Process (a)

14.4 g (0.1 mol) of 2-methyl-pyran-2-carboxylic acid and 10.1 g (0.1 mol) of triethylamine are dissolved in 100 ml of tetrahydrofuran. 10.85 g (0.1 mol) of ethyl chloroformate are added dropwise to this solution at 5° C. to 10° C. with cooling, and the mixture is stirred for a further 2 hours at room temperature. 23.0 g (0.1 mol) of 4-(4,6-dimethyl-pyridyl-2-thio)-aniline are then introduced. The mixture is stirred for 1 hour at room temperature, boiled under reflux for 2 hours, and, after cooling, stirred into 1 l of icewater. The crystals which separate are filtered off under suction and dried in air.

27.4 g (77% of theory) of 4'-(4,6-dimethyl-pyridyl2-thio)-2-methyl-pyran-2-carboxanilide of melting point 107° C. to 109° C. (recrystallized from washing benzine) are obtained.

Example 4

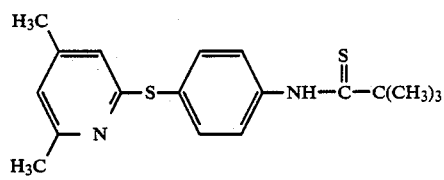

23.89 g (76 mmol) of 4'-(4,6-dimethyl-pyridyl-2-thio)-pivalanilide and 16.72 g (41.8 mmol) of Lawesson reagent are refluxed in 76 ml of absolute toluene, the course of he reaction being followed by TLC. The mixture is cooled to room temperature and filtered on silica gel with toluene/acetone 20:1. The solution is evaporated, and the residue crystallized from ethyl acetate/n-hexane. 15.98 g (63.6% of theory) of pivaloylthio-4-(4,6-dimethyl-pyridyl-2-thio)-anilide of melting point 127° C. are obtained.

The compounds of the formula (Ia) or (Ib) listed in the following Table 2 are obtained in a corresponding fashion and according to the general information for the preparation:

TABLE 2

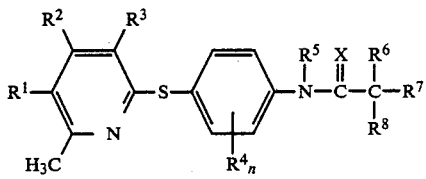

| Ex. No. | R¹ | R² | R³ | R⁴ | n | R⁵ | X | R⁶ | R⁷ | R⁸ | M.p./°C |
|---|---|---|---|---|---|---|---|---|---|---|---|
| 5 | H | H | H | — | 0 | H | O | $CH_3$ | $CH_3$ | $CH_3$ | 170–172 |
| 6 | H | H | H | — | 0 | H | O | $CH_2Cl$ | $CH_3$ | $CH_3$ | 138–140 |
| 7 | H | H | H | — | 0 | H | O | $CH_3$ | —$(CH_2)_4$— | | 124–126 |
| 8 | H | $CH_3$ | H | — | 0 | H | O | H | $C_2H_5$ | $C_2H_5$ | 152–154 |
| 9 | H | $CH_3$ | H | — | 0 | H | O | $CH_3$ | $CH_3$ | $CH_3$ | 156–157 |
| 10 | H | $CH_3$ | H | — | 0 | H | O | $CH_2Cl$ | $CH_3$ | $CH_3$ | 144–145 |
| 11 | H | $CH_3$ | H | — | 0 | H | O | $C_2H_5$ | $CH_3$ | $CH_3$ | 137–139 |
| 12 | H | $CH_3$ | H | — | 0 | H | O | $C_3H_7$ | $CH_3$ | $CH_3$ | 75–76 |
| 13 | H | $CH_3$ | H | — | 0 | H | O | $CH(CH_3)_2$ | $CH_3$ | $CH_3$ | 130–132 |
| 14 | H | $CH_3$ | H | — | 0 | H | O | CN | $CH_3$ | $CH_3$ | 134–136 |
| 15 | H | $CH_3$ | H | — | 0 | H | O | $CH_3$ | —$(CH_2)_5$— | | 108–109 |
| 16 | H | $CH_3$ | H | — | 0 | H | O | —O—$(CH_2)_4$— | $CH_3$ | | 107–109 |
| 17 | H | $CH_3$ | CN | — | 0 | H | O | $CH_3$ | $CH_3$ | $CH_3$ | 153–155 |
| 18 | H | $CH_3$ | CN | — | 0 | H | O | $C_2H_5$ | $CH_3$ | $CH_3$ | 174–176 |
| 19 | H | $CH_3$ | CN | — | 0 | H | O | $CH_3$ | —$(CH_2)_5$— | | 128–130 |
| 20 | H | $CH_3$ | CN | 3-Cl | 1 | H | O | $CH_3$ | $CH_3$ | $CH_3$ | 162–164 |
| 21 | H | $CH_3$ | H | — | 0 | H | S | $CH_3$ | $CH_3$ | $C_2H_5$ | 76 |
| 22 | H | $CH_3$ | H | — | 0 | H | S | $CH_3$ | $CH_3$ | $i$-$C_3H_7$ | 99 |

Example 23

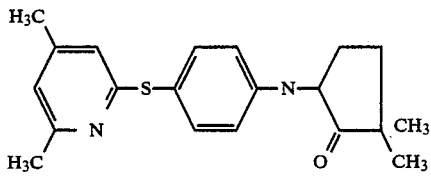

melting point: 134° C.

Example 24

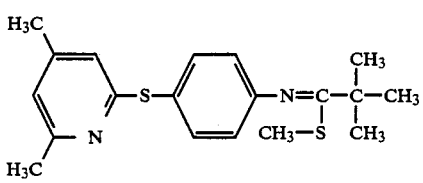

Process (c)

2.02 g (18 mmol) of potassium tert. butylate are added to 4.96 g (15 mmol) of pivaloylthio-4-(4,6-dimethyl-pyridyl-2-thio)-anilide in 60 ml of tert. butanol at 50° C., the mixture is stirred for 15 minutes and after adding 1.1 ml (18 mmol) of methyl iodide is stirred while being monitored by thin-layer chromatography. The reaction mixture is stirred into 200 ml of water and the reaction product is extracted with ethyl acetate. The organic phase is dried and the solvent distilled off in vacuo. The residue is chromatographed (column chromatography) with cyclohexane/ethyl acetate (3:1) and recrystallized in n-hexane.

3.6 g (69.7% of theory) of the desired product with a melting point of 78° C. are obtained.

Example 25

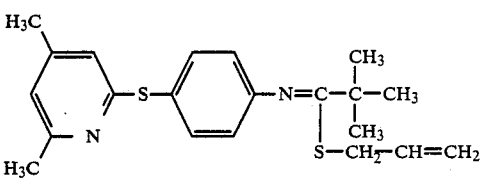

melting point: 43° C.

This compound is prepared by the same method as that described in Examaple 24.

PREPARATION OF THE STARTING MATERIALS

Example II-1

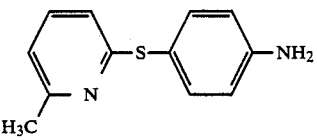

12.5 g (0.1 mol) of 4-amino-thiophenol are dissolved in 50 ml of tetramethylene sulphone. 5.6 g (0.1 mol) of powdered potassium hydroxide are added in portions to this solution. The mixture is stirred for 30 minutes at room temperature, 12.75 g (0.1 mol) of 2-chloro-6-methyl-pyridine are subsequently added, and the mixture is then heated for 5 hours at 120° C. to 130° C. After cooling, the reaction mixture is poured into 1 l of ice-water. The crystals which separate are filtered off under suction and dried in air.

17.8 g (8.24% of theory) of 4-(6-methyl-pyridyl-2-thio)-aniline of melting point 72° C. to 74° C. (recrystallized from carbon tetrachloride) are obtained.

The following are obtained in a corresponding fashion:

II-2: 4-(4,6-dimethyl-pyridyl-2-thio)-aniline:

M.p. 108° C. to 110° C. (recrystallized from carbon tetrachloride)

II-3: 4-(4,6-dimethyl-3-cyano-pyrdyl-2-thio)-aniline;

M.p. 144° C. to 146° C. (recrystallized from toluene)

II-4: 3-chloro-4-(4,6-dimethyl-3-cyano-pyridyl-2-thio)-aniline;

M.p. 163° C. to 165° C. (recrystallized from toluene).

Example A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

In this test, the compounds according to preparation Examples 1, 9, 10, 12, 13 and 14, exhibit a very good herbicidal action particularly in Amaranthus and Chenopodium, along with very good crop plant compatibility particularly on wheat and corn.

It is understood that the specification and examples are illustrative but not limitative of the present invention and that other embodiments within the spirit and scope of the invention will suggest themselves to those skilled in the art.

We claim:

1. A pyridylthio-acetanilide of the formula

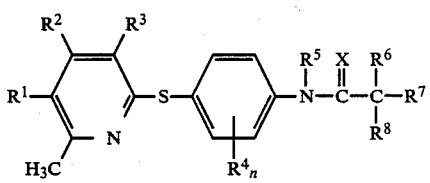

in which $R^1$, $R^2$ and $R^3$, independently of one another, represent hydrogen, fluorine, chlorine, bromine, cyano or trifluoromethyl, or alkyl, alkoxy or alkylthio having 1 to 4 carbon atoms in each case, $R^4$ represents fluorine, chlorine, bromine, methyl or methoxy, n represents a number 0, 1 or 2, $R^5$ represents hydrogen, or alkyl having 1 to 4 carbon atoms, or alkenyl or alkinyl having 2 to 6 carbon atoms in each case, $R^6$ represents hydrogen, fluorine, chlorine, bromine, cyano, alkyl, having 1 to 4 carbon atoms, which is optionally mono- or polysubstituted identically or differently by fluorine, chlorine or bromine, alkenyl having 2 to 4 carbon atoms, phenyl or benzyl which are in each case optionally mono- to pentasubstituted identically or differently by fluorine, chlorine, bromine, trifluoromethyl, methyl and methoxy, or represent the $-OR^{12}$ or $-S(O)_m-R^{12}$ radicals, where $R^{12}$ represents alkyl having 1 to 4 carbon atoms which is optionally mono- or polysubstituted identically or differently by fluorine, chlorine, bromine, methoxy or ethoxy, or represent phenyl which is optionally mono- to pentasubstituted identically or differently by fluorine, chlorine, bromine or $C_1$-$C_4$alkyl, m represents a number 0, 1 or 2, $R^7$ ad $R^8$, independently of one another, represent fluorine, chlorine, bromine or alkyl having 1 to 4 carbon atoms which is optionally mono- or polysubstituted identically or differently by fluorine, chlorine or bromine, X represents oxygen or sulphur.

2. A compound according to claim 1, wherein such commpound is 4'-(4,6-dimethyl-pyridyl-2-thio)-pivalanilide of the formula

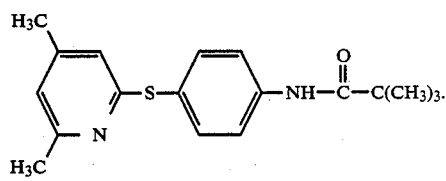

3. A compound according to claim 1, wherein such compound is 4'-(4,6-dimethyl-pyridyl-2-thio)-2-chloromethyl-propane-2-carboxanilide of the formula

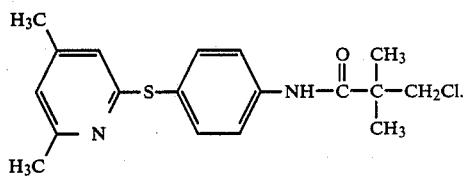

4. A compound according to claim 1, wherein such compound is 4'-(4,6-dimethyl-pyridyl-2-thio)-2-methyl-pentane-2-carboxanilide of the formula

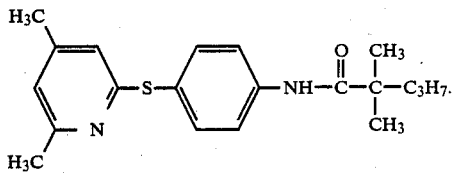

5. A compound according to claim 1, wherein such compound is 4'-(4,6-dimethyl-pyridyl-2-thio)-2,3-dimethylbutane-2-carboxanilide of the formula

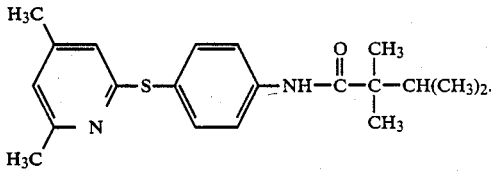

6. A compound according to claim 1, wherein such compound is 4'-(4,6-dimethyl-pyridyl-2-thio)-2-cyano-propane-2-carboxanilde of the formula

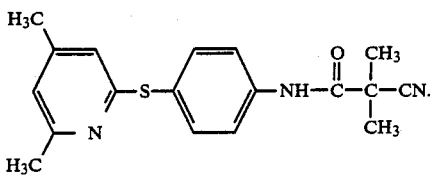

7. A herbicidal composition comprising a herbicidally effective amount of a compound according to claim 1 and a diluent.

8. A method of combating unwanted vegetation which comprises applying to such vegetation or to a locus from which it is desired to exclude such vegetation a herbicidally effective amount of a compound according to claim 1.

9. The method according to claim 8, wherein such compound is
- 4'-(4,6-dimethyl-pyridyl-2-thio)-pivalanilide,
- 4'-(4,6-dimethyl-pyridyl-2-thio)-2-chloromethylpropane-2-carboxanilide,
- 4'-(4,6-dimethyl-pyridyl-2-thio)-2-methyl-pentane-2-carboxanilide,
- 4'-(4,6-dimethyl-pyridyl-2-thio)-a,3-dimethylbutane-2-carboxanilide or
- 4'-(4,6-dimethyl-pyridyl-2-thio)-2-cyanopropane-2-carboxanilide.

* * * * *